US012614611B2

(12) United States Patent
Mande et al.

(10) Patent No.: US 12,614,611 B2
(45) Date of Patent: *Apr. 28, 2026

(54) METHOD AND SYSTEM FOR IDENTIFICATION OF CANDIDATE TARGET SITES FOR COMBATING PATHOGENS

(71) Applicant: Tata Consultancy Services Limited, Mumbai (IN)

(72) Inventors: Sharmila Shekhar Mande, Pune (IN); Swadha Anand, Pune (IN); Preethi Alagarai Sampath, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1108 days.

This patent is subject to a terminal disclaimer.

(21) Appl. No.: 17/615,657

(22) PCT Filed: Jun. 5, 2020

(86) PCT No.: PCT/IB2020/055308

§ 371 (c)(1),
(2) Date: Dec. 1, 2021

(87) PCT Pub. No.: WO2020/245783

PCT Pub. Date: Dec. 10, 2020

(65) Prior Publication Data

US 2022/0310204 A1 Sep. 29, 2022

(30) Foreign Application Priority Data

Jun. 6, 2019 (IN) ............................ 201921022523

(51) Int. Cl.

| | |
|---|---|
| ***G16B 30/00*** | (2019.01) |
| ***C12N 9/22*** | (2006.01) |
| ***C12N 15/11*** | (2006.01) |
| ***C12N 15/74*** | (2006.01) |
| ***C12Q 1/689*** | (2018.01) |

(52) U.S. Cl.

CPC ............... *G16B 30/00* (2019.02); *C12N 9/22* (2013.01); *C12N 15/111* (2013.01); *C12N 15/74* (2013.01); *C12Q 1/689* (2013.01); *C12N 2310/20* (2017.05)

(58) Field of Classification Search

None

See application file for complete search history.

(56) References Cited

U.S. PATENT DOCUMENTS

| | | | |
|---|---|---|---|
| 6,783,985 | B1 | 8/2004 | Roemer et al. |
| 2005/0019931 | A1 | 1/2005 | Roemer et al. |
| 2012/0004111 | A1 | 1/2012 | Colwell et al. |
| 2016/0022797 | A1 | 1/2016 | Tang |
| 2017/0087237 | A1 | 3/2017 | Gunn et al. |
| 2017/0327565 | A1 | 11/2017 | Schrader |
| 2019/0021343 | A1 | 1/2019 | Barrangou et al. |

OTHER PUBLICATIONS

Kisselev, Lev. “Polypeptide release factors in prokaryotes and eukaryotes: same function, different structure.” Structure 10.1 (2002): 8-9.*

Witkowski, Andrzej, et al. “Conversion of a β-ketoacyl synthase to a malonyl decarboxylase by replacement of the active-site cysteine with glutamine.” Biochemistry 38.36 (1999): 11643-11650.*

Whisstock, James C., and Arthur M. Lesk. “Prediction of protein function from protein sequence and structure.” Quarterly reviews of biophysics 36.3 (2003): 307-340.*

Devos, Damien, and Alfonso Valencia. “Practical limits of function prediction.” Proteins: Structure, Function, and Bioinformatics 41.1 (2000): 98-107.*

Bhatt et al., “FLIM-MAP: Gene Context Based Identification of Functional Modules in Bacterial Metabolic Pathways,” Frontiers in Microbiology, vol. 9, Article 2183 (2018).

Bouchery et al., “Exploiting Old Pathogens to Create New Therapeutics,” Cell Host & Microbe, 20 (2016).

Gomaa et al., “Programmable Removal of Bacterial Strains by Use of Genome-Targeting CRISPR-Cas Systems,” mBio 5(1):e00928-13 (2014).

Roemer et al., “Large-scale essential gene identification in Candida albicans and applications to antifungal drug discovery,” Molecular Microbiology, 50(1):167-181 (2003).

* cited by examiner

*Primary Examiner* — G. Steven Vanni

(74) *Attorney, Agent, or Firm* — Finnegan, Henderson, Farabow, Garrett & Dunner, LLP

(57) ABSTRACT

A system and method for identification of target sites in a pathogenic genome and combating a pathogenic infection have been provided. The present disclosure utilizes the fact that a conserved stretch of nucleotide sequence in genomic neighborhood of genes important for bacteria can be targeted to disrupt the overall functioning of the pathogen. The method involves identification of nucleotide repeat sequences in the DNA. The method and system also involve administration of a cocktail comprising antimicrobial drugs, biofilm inhibitors and a construct. The genomic neighborhood or vicinity or ‘flanking genes’ refers to regions lying within a predefined number of genes to the identified conserved stretch of nucleotide repeat sequence (or its reverse complement) on the candidate pathogen genome or within a distance of predefined number of bases with respect to the conserved stretch of nucleotide repeat sequence (or its reverse complement) on the candidate pathogen genome.

12 Claims, 9 Drawing Sheets

Specification includes a Sequence Listing.

200

Start

Obtain a sample from an infected area — 202

Extract DNA from the obtained sample using DNA extraction methods — 204

Sequence the isolated DNA using a sequencer — 206

Detect the pathogen from the sequenced DNA — 208

Identify a set of nucleotide repeat sequences in the extracted DNA which are occurring more than a predefined number of times in the pathogen genome — 210

Identify a set of neighborhood genes present upstream and downstream of the set of nucleotide repeat sequences — 212

Categorize the set of neighborhood genes according to their functional roles in the pathogen based on their involvement in pathways — 214

Test the presence of a secondary structure in identified set of nucleotide sequences — 216

Administer an engineered polynucleotide construct on the infected area depending on the presence of the secondary structure to treat the pathogenic infection to cleave the set of nucleotide repeat sequences and removal of flanking genes, wherein the engineered polynucleotide construct is comprising: one or more of the set of nucleotide sequences with repeats of multiple copies dispersed in nucleotide sequences of genomes, a first enzyme capable of nicking and cleaving the identified set of nucleotide sequences, and a second enzyme capable of removal of set of neighborhood genes flanking set of nucleotide repeat sequences — 218

Check the efficacy of the administered engineered polynucleotide construct to combat the antibiotic induced pathogens after a predefined time period — 220

Re-administer the engineered polynucleotide construct if the antibiotic induced pathogens are still present after checking in the infected area — 222

Stop

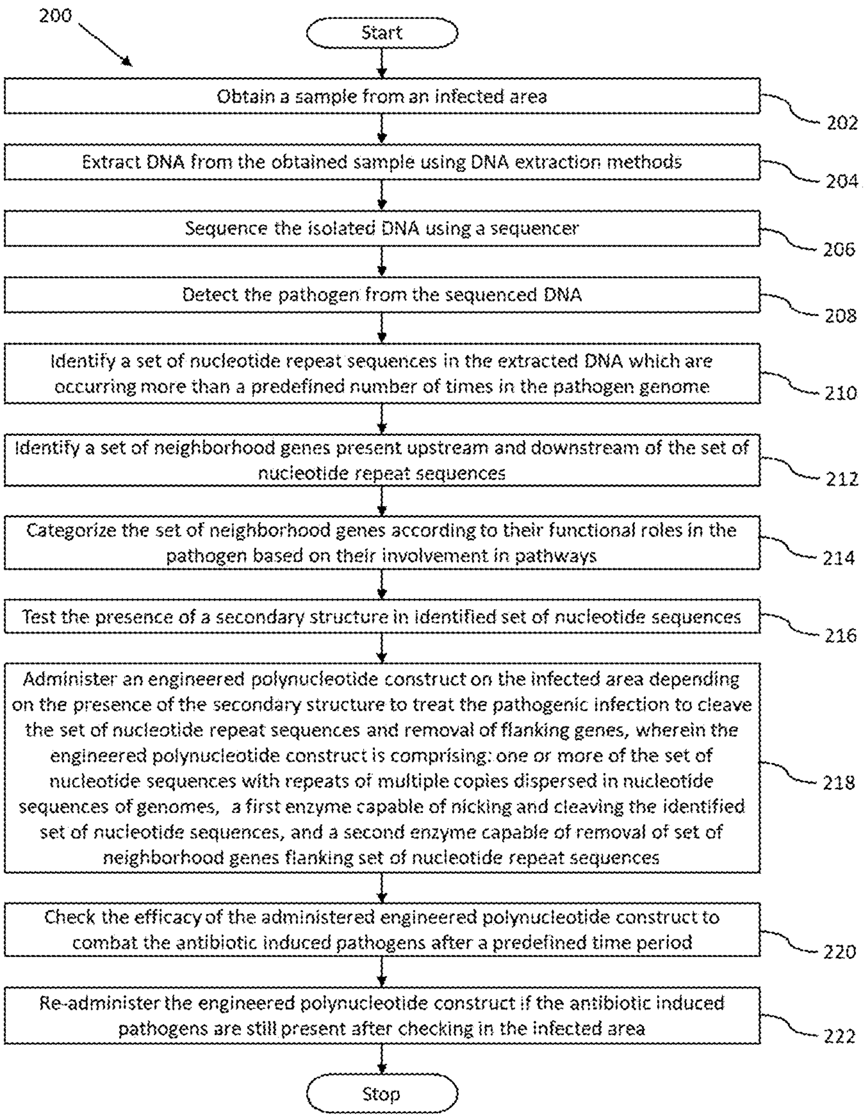

FIG. 3

| | | |
|---|---|---|
| �nnn | > | R-ELEMENT 1 |
| ▨ | > | R-ELEMENT 2 |
| ▧ | > | ENZYME 1 |
| ▩ | > | ENZYME 2 |

SEQUENCE LISTING

```
<160> NUMBER OF SEQ ID NOS: 1

<210> SEQ ID NO 1
<211> LENGTH: 41
```

-continued

```
<212> TYPE: DNA
<213> ORGANISM: Streptococcus pneumoniae
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (14)..(28)
<223> OTHER INFORMATION: n is a, c, g, or t
<220> FEATURE:
<221> NAME/KEY: VariableLength
<222> LOCATION: (18)..(28)
<223> OTHER INFORMATION: Nucleotide residues in these positions may be
      present or absent
<220> FEATURE:
<221> NAME/KEY: misc_feature
<222> LOCATION: (35)..(36)
<223> OTHER INFORMATION: n is a, c, g, or t

<400> SEQUENCE: 1

gyatmnwrtc argnnnnnnn nnnnnnnnyt tgatnnkatr c                           41
```

METHOD AND SYSTEM FOR IDENTIFICATION OF CANDIDATE TARGET SITES FOR COMBATING PATHOGENS

PRIORITY CLAIM

The present application is a U.S. National Stage Filing under 35 U.S.C. § 371 and claims priority from International Application No. PCT/IB2020/055308, filed on Jun. 4, 2020, which application claims priority from Indian Provisional Patent Application No. 201921022523, filed on Jun. 6, 2019. The entire contents of the aforementioned application are incorporated herein by reference.

TECHNICAL FIELD

The embodiments herein generally relate to the field of pathogenic infection in a pathogenic genome, and, more particularly, to a method and system for identification of target sites in the pathogenic genome.

BACKGROUND

Infectious diseases caused by pathogenic bacteria pose a serious threat to the health sector across the world. The most common method of treating such infections is the use of antibiotics. However, the rampant use of these has led to development of antibiotic resistance in most pathogens. In an antimicrobial resistance review conducted in 2014, it was estimated that about 10 million people will die of antimicrobial resistance (AMR) associated diseases by 2050 (e.g., refer Antimicrobial Resistance: Tackling a crisis for the health and wealth of nations. The Review on Antimicrobial Resistance, chaired by Jim O'Neill. 2014 December). Accordingly, CDC (Center for Disease Control and Prevention, U.S. Dept. of Health and Human Services) has classified infectious bacteria into Urgent, Serious and Concerning threats based on the prevalence of drug-resistance in them (e.g., refer Antibiotic Resistance Threats in United States, 2013, CDC Report.).

The issue of antimicrobial resistance is compounded by the fact that these antibiotic resistance genes can be transferred from one bacterium to another utilizing several transfer methods. Additional problems arise which pertain to formation of biofilms in these bacteria which allow them to evade antibiotics. Several studies have shown that biofilm formation inhibitors (like several enzymes which degrade the matrix) as well as quorum quenchers (which prevent biofilm formation) can prove useful in this regard. Despite utilizing these inhibitors, several bacteria still escape the antibiotics and lead to relapse once the treatment is stopped. Conventionally known methods have been utilized to disrupt biofilms or prevent their formation. Various enzymes such as lysostaphin, palmitoelic acid and various other peptidases, amylases and ligases have been used to disrupt the biofilms after which antibacterial agents are used. Further, several quorum quenchers like acyl homoserine lactones have also been used to disrupt the quorum sensing machinery of pathogens. However, studies show that bacteria are capable of developing resistance to these biofilm inhibitors using certain efflux pumps to remove the compound out of their cytoplasm (e.g., refer Garcia-Contreras, Rodolfo, Toshinari Maeda, and Thomas K. Wood. "Resistance to quorum-quenching compounds." Applied and environmental microbiology 79.22 (2013): 6840-6846).

Another known method involves utilizing mechanisms to elicit an immune response in host against several antigenic/virulent proteins. Yet another known method uses antisense oligomers based silencing mechanism to impede functioning of certain genes in pathogens. Additionally, antibacterial agents are introduced into bacteriophages which can specifically target these pathogenic bacteria. Infectious bacteria can evade all of these methods of treatment by mutating certain key proteins or factors, thereby rendering the therapeutic strategy ineffective.

SUMMARY

Embodiments of the present disclosure present technological improvements as solutions to one or more of the above-mentioned technical problems recognized by the inventors in conventional systems. For example, in one embodiment, a system for identification of candidate target sites for combating pathogenic infection is provided. The system comprises a sample collection module, a pathogen detection and DNA extraction module, a sequencer, one or more hardware processor, a memory, an administration module and an efficacy module in communication with the one or more hardware processors. The sample collection module obtains a sample from an infected area. The pathogen detection and DNA extraction module isolates DNA from the obtained sample using one of a laboratory methods or DNA isolation kits. The sequencer sequences the isolated DNA. The one or more first hardware processors are configured to execute programmed instructions stored in the one or more first memories, to: identify a set of nucleotide repeat sequences in the extracted DNA which are occurring more than a predefined number of times in the pathogen genome; identify a set of neighborhood genes present upstream and downstream of the set of nucleotide repeat sequences; categorize the set of neighborhood genes according to their functional roles in the pathogen based on their involvement in pathways; test the presence of a secondary structure in the identified set of nucleotide sequences. The administration module prepares and administers an engineered polynucleotide construct on the infected area depending on the presence of the secondary structure of the identified nucleotide repeat to treat the pathogenic infection to cleave the set of nucleotide repeat sequences and removal of flanking genes, wherein the engineered polynucleotide construct is comprising: one or more of the set of nucleotide repeat sequences of multiple copies at dispersed locations on the genomes, a first enzyme capable of nicking and cleaving the identified set of nucleotide sequences, and a second enzyme capable of removal of a set of neighborhood genes flanking the set of nucleotide repeat sequences. The efficacy module assesses the efficacy of the administered construct and re-administers the engineered polynucleotide construct repetitively in case the pathogen presence is detected at the infected area post administering.

In another aspect, a method for identification of candidate target sites for combating pathogenic infection is provided. Initially, a sample is obtained from an infected area. Further, DNA is extracted from the obtained sample using DNA extraction methods. Later, the isolated DNA is sequenced using a sequencer. In the next step, the pathogen is detected from the sequenced DNA. Further, a set of nucleotide repeat sequences is identified in the extracted DNA which are occurring more than a predefined number of times in the pathogen genome. Later, a set of neighborhood genes is identified present upstream and downstream of the set of nucleotide repeat sequences. In the next step, the set of neighborhood genes is categorized according to their functional roles in the pathogen based on their involvement in pathways. The presence of a secondary structure is then tested in the identified set of nucleotide sequences. In the next step, an engineered polynucleotide construct is administered on the infected area to treat the pathogenic infection by cleaving the set of nucleotide repeat sequences and removal of flanking genes, wherein the engineered polynucleotide construct is comprising: one or more of the set of nucleotide repeat sequences occurring in multiple copies at dispersed locations on the candidate pathogen genomes, a first enzyme capable of nicking and cleaving the identified set of nucleotide repeat sequences, and a second enzyme capable of removal of a set of neighborhood genes flanking the set of nucleotide repeat sequences. Further, the efficacy of the administered construct is assessed. And finally, the engineered polynucleotide construct is re-administered repetitively in case the pathogen presence is detected at the infected area post administering.

The target sites or nucleotide repeat sequences in this disclosure refer to nucleotide sequences which repeat a minimum number of ten times within the genome of the candidate pathogen/pathogens which are identified in an infected site from which the sample is collected. These nucleotide repeat sequences can be targeted in order to debilitate the pathogen. The mentioned nucleotide repeat sequence/sequences is selected if it occurs more than 10 times in all the strains of the candidate species or genus to which the candidate pathogen/pathogens identified in an infected site belong. The nucleotide repeat sequence is selected such that it does not occur more than twice in genomes of strains belonging to any other genus than that of the candidate pathogen and does not occur more than twice within the genome of the host.

In yet another aspect, one or more non-transitory machine readable information storage mediums comprising one or more instructions which when executed by one or more hardware processors cause identification of candidate target sites for combating pathogenic infection. Initially, a sample is obtained from an infected area. Further, DNA is extracted from the obtained sample using DNA extraction methods. Later, the isolated DNA is sequenced using a sequencer. In the next step, the pathogen is detected from the sequenced DNA. Further, a set of nucleotide repeat sequences is identified in the extracted DNA which are occurring more than a predefined number of times in the pathogen genome. Later, a set of neighborhood genes is identified present upstream and downstream of the set of nucleotide repeat sequences. In the next step, the set of neighborhood genes is categorized according to their functional roles in the pathogen based on their involvement in pathways. The presence of a secondary structure is then tested in the identified set of nucleotide sequences. In the next step, an engineered polynucleotide construct is administered on the infected area to treat the pathogenic infection by cleaving the set of nucleotide repeat sequences and removal of flanking genes, wherein the engineered polynucleotide construct is comprising: one or more of the set of nucleotide repeat sequences occurring in multiple copies at dispersed locations on the candidate pathogen genomes, a first enzyme capable of nicking and cleaving the identified set of nucleotide repeat sequences, and a second enzyme capable of removal of a set of neighborhood genes flanking the set of nucleotide repeat sequences. Further, the efficacy of the administered construct is assessed. And finally, the engineered polynucleotide construct is re-administered repetitively in case the pathogen presence is detected at the infected area post administering.

It is to be understood that both the foregoing general description and the following detailed description are exemplary and explanatory only and are not restrictive of the invention, as claimed.

BRIEF DESCRIPTION OF THE DRAWINGS

The embodiments herein will be better understood from the following detailed description with reference to the drawings, in which:

FIG. 3 illustrates a flowchart showing steps involved in identification of candidate target sites for combating pathogenic infection according to an embodiment of the present disclosure.

DETAILED DESCRIPTION OF EMBODIMENTS

Figure 1:
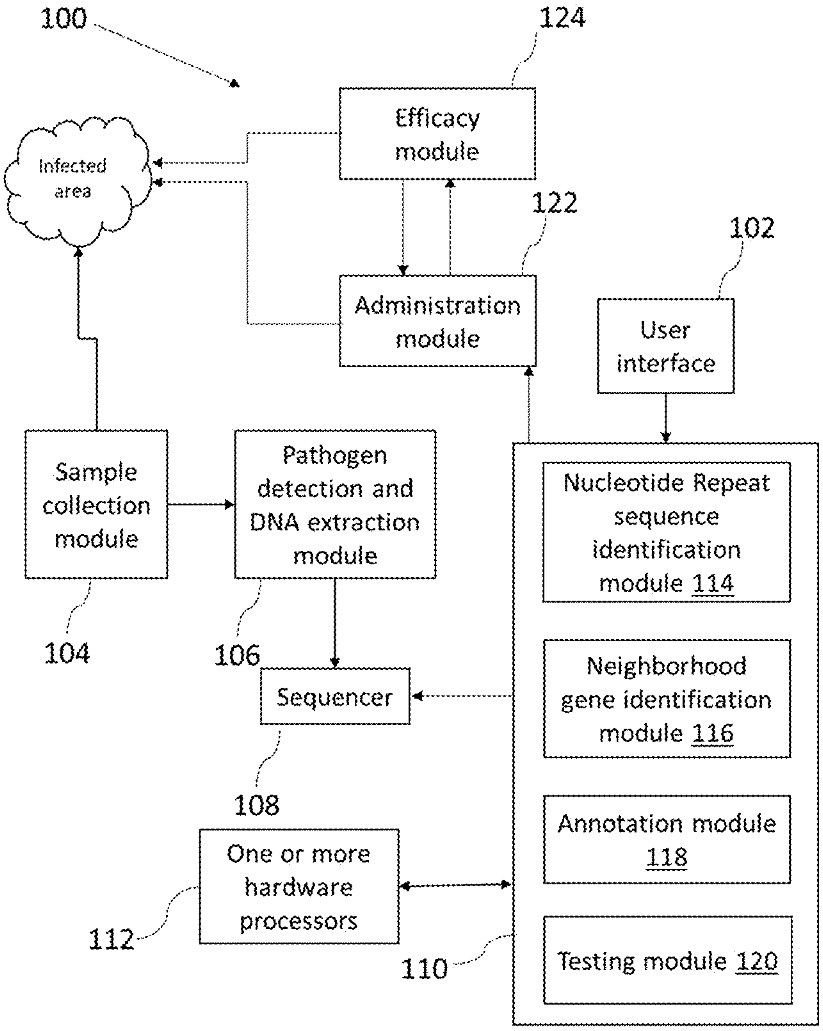
FIG. 1 illustrates a block diagram of a system for identification of candidate target sites for combating pathogenic infection according to an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Glossary—Terms Used in the Embodiments

The expression "repeated nucleotide sequences" or "the set of nucleotide repeats" or "target sequence" or "target sites" or "repeated sequence regions" or "similar sequence stretches" or "target nucleotide repeat sequence" or "conserved stretch of nucleotide sequences" or "repeat element"

in the context of the present disclosure refers to nucleotide sequences or stretches of nucleotide sequences which have been repeated multiple times in a sequence of DNA extracted from a sample obtained from a sample obtained from the infected area or within nucleotide sequence obtained for a genomic sequence of a pathogen or genomic sequences of strains belonging to a pathogenic genus or species.

The term "metagenome refers" to the genetic material derived directly from the infected site and can be considered representative of overall microorganisms present in a sample collected from an environment. The information about metagenome and its taxonomic constitution is obtained by either sequencing the genes considered as markers for different taxa (for example 16S rRNA), amplifying genes of interest using specific primers through methods like but not limited to Polymerase Chain Reaction (PCR). This information can also be obtained by whole genome sequencing of the obtained environmental or metagenomic sample. The sample collected from the environment is referred to from now on as metagenomic sample.

The term "identified nucleotide repeat sequence is dispersed across distant locations in the pathogen genome" refers to the fact that the nucleotide sequences identified in this method are spread across distant locations on the pathogen genome and is not clustered together at one particular location alone on the genome.

In this disclosure, the terms "distant location" or "distinct location" or "dispersed location" refer to locations of two nucleotide repeat sequences that are separated by more than 10000 base pairs. Nucleotide repeat regions having distances less than 10000 base pairs between their locations have been considered as clustered repeats.

The expression "candidate genus" or candidate pathogen refers to the genus, species or pathogen in which the nucleotide repeat sequence is identified which is used as a target sequence site.

The term "commensal" refers to microbe/microbes which are considered beneficial to the host or cause no harm to the host.

The term 'pathogen' refers to microbe/microbes which cause a disease in host.

The term 'host' refers to either a living organism or an environmental site. In an embodiment, 'host' may refer to human, animal or plant in which a pathogenic infection may be observed.

The term 'non-culturable' refers to microbes that cannot be grown in a laboratory settings because the ideal conditions and media for their growth is not well characterized. Such microbes can be analyzed by culture independent methods discussed in various embodiments of the disclosure.

Majority of the existing methods for combating pathogens focus on silencing specific genes in order to curtail their expression. Targeting single functional aspects of bacteria often is not sufficient as bacteria might mutate the targets and develop resistance to the therapeutic intervention. To overcome the drawbacks of the existing methods, the present system and method deals with identifying and targeting multiple copies of a nucleotide repeat sequence at distant locations on the genome as well as the important functional genes flanking this sequence. Therefore, the method allows to debilitate multiple important functions of the pathogen simultaneously. The important functional genes in this disclosure refer to the genes in pathogens which encode for proteins which are critical for survival, pathogenicity, interaction with the host, adherence to the host or for the virulence of bacteria. Development of resistance in pathogens to the method mentioned in this disclosure is difficult as the pathogen will have to bring about multiple mutations in distant locations on the pathogen genome. The cocktail comprising antimicrobial drugs, biofilm inhibitors and the novel sequence based therapy described in the disclosure combats the infection. To overcome the drawbacks discussed in the background section, the present disclosure includes targeting multiple virulence and essential proteins of pathogens in addition to antimicrobials and biofilm inhibitors. The method may also include targeting various other proteins performing important functions (metabolism, host interactions, pathogenicity etc.) in bacteria.

Referring now to the drawings, and more particularly to FIG. 1 through FIG. 9, where similar reference characters denote corresponding features consistently throughout the figures, there are shown preferred embodiments and these embodiments are described in the context of the following exemplary system and/or method.

According to an embodiment of the disclosure, a system 100 for identification of target sites in a pathogenic genome and treating a pathogenic infection is shown in the block diagram of FIG. 1. The present disclosure utilizes the fact that a conserved stretch of nucleotide sequence in genomic neighborhood of genes important for bacteria (e.g. virulence factors, survival/essential genes) can be targeted to disrupt the overall functioning of the pathogen. The method involves identification of nucleotide repeat sequences in the DNA. The method and system also involve administration of a cocktail comprising antimicrobial drugs, biofilm inhibitors and a construct described in this disclosure. In the present disclosure genomic neighborhood or vicinity or 'flanking genes' refers to regions lying within a predefined number of genes to the identified conserved stretch of nucleotide repeat sequence (or its reverse complement) on the candidate pathogen genome or within a distance of predefined number of bases with respect to the conserved stretch of nucleotide repeat sequence (or its reverse complement) on the candidate pathogen genome. The flanking genes are found on each strand on pathogen genomic DNA. In an embodiment the genomic neighborhood or flanking genes may comprise of 10 genes lying on either side of identified conserved stretch of nucleotide repeat sequence or its reverse complement in terms of its location on the pathogen genome. The reverse complement of target sequence is obtained by interchanging letters A and T and interchanging letters C and G between target and complement sequence.

According to an embodiment of the disclosure, the system 100 consists of a user interface 102, a sample collection module 104, a pathogen detection and DNA extraction module 106, a sequencer 108, a memory 110 and one or more hardware processors (referred as a processor, herein after) 112 as shown in FIG. 1. The processor 112 is in communication with the memory 110. The memory 110 further includes a plurality of modules for performing various functions. The memory 110 may include a nucleotide repeat sequence identification module 114, a neighborhood gene identification module 116, an annotation module 118 and a testing module 120. The system 100 further comprises an administration module 122 and an efficacy module 124 as shown in the block diagram of FIG. 1.

According to an embodiment of the disclosure, a method for identification of target sites in a pathogenic genome is disclosed. According to the present method a strategy is adopted which targets the pathogen genome in multiple places/locations and provides access to multiple important proteins in a pathogen. In one of the embodiments, the present method utilizes the fact that multiple occurrences of a conserved stretch of nucleotide sequence occurring multiple times on a candidate pathogen genome, which is in genomic neighborhood of genes encoding virulence factors or in vicinity of genes essential for survival encoded within a genome of the candidate pathogen may be targeted to disrupt the overall genetic machinery of the pathogen. These nucleotide repeat sequences might also lie in the neighborhood of genes which perform other critical functions in a pathogen. A conserved stretch of sequence refers to a nucleotide repeat sequence which occurs within all pathogenic genomes belonging to a candidate genus. Another important factor considered is occurrence of the conserved stretch of sequences only in genomic sequences of pathogenic strains of the candidate pathogen and minimum cross-reactivity with the commensals belonging to same candidate genus or other genera as well as the host. Cross-reactivity, in this disclosure, refers to the occurrence of these conserved stretches of nucleotide sequences more than twice in genera/species other than the candidate genus/species or more than twice within commensal bacteria belonging to the candidate genus for which this sequence is being utilized as a target. The nucleotide repeat sequence should not occur more than twice in the host genome also. Further, the identified potential target sites in pathogen are not specific to a single strain of the pathogen. In most cases, metagenomic samples contain bacteria whose strain level information cannot be obtained. Thus, the method can be utilized to target all pathogenic strains of pathogens in the given species/genera of the pathogen and is not hindered by the absence of strain level information. Thus, the first step involved is identification of a consensus sequence region, which occurs multiple times on a genome and is specific to particular pathogenic genus only. Following is a brief description of the aforementioned methodology.

The method involves identifying nucleotide sequence stretches which repeat multiple times on a pathogen genome G belonging to Genus Ge and are dispersed at distant locations on the pathogen genome G. These stretches were aligned within the same genome by local alignment (as implemented in PILER software (e.g., refer Edgar, Robert C., and Eugene W. Myers. "PILER: identification and classification of genomic repeats." Bioinformatics 21. suppl_1 (2005): i152-i158) to find the location of these elements and the number of times these sequence stretches repeat across the pathogen genomes belonging to candidate genus Ge. Similar search was carried on other sequenced pathogen genomes belonging to Genus Ge to confirm conservation of candidate identified sequence across all pathogenic strains of Genus Ge. Further, the candidate sequence is aligned to genomes belonging to genera other than Ge and is confirmed that there are no more than two matches on any of these genomes to rule out cross-reactivity. Cross-reactivity, in this disclosure, refers to the occurrence of these conserved stretches of nucleotide sequences more than twice in genera other than the candidate genus for which this sequence is being utilized as a target. Sequence based search utilizing any other sequence alignment or repeat finding tools is within scope of the present disclosure. Herein, if the number of times Rn matches on the genomes of Genus Ge is greater than the predefined threshold (refers to the number of occurrences of nucleotide repeat sequence on a genome in a dispersed manner and this number might vary with system and pathogen under consideration minimum number of occurrences being 10) and Rn does not match any other genome of genera other than Ge more than two times (no cross reactivity), the sequence stretch is termed as R-ELEMENT. If R-ELEMENT is palindromic, case I is followed, else case II is followed. Case I and Case II are described in detail in the subsequent paragraphs.

Identification and functional annotation of gene neighborhood of R-ELEMENT was performed. In here, on each genome G of Genus Ge where R-ELEMENT occurs, flanking genes on either side and on each strand of Genome G was determined. In this embodiment, flanking genes refer to the genes surrounding the identified repeat sequence on the genome. In this embodiment, 10 flanking genes were included but the span may vary with each pathogen and system. Functional annotation of these genes which in this embodiment was performed using HMM search but use of any other annotation methods (PSSM, BLAST etc.) is within scope of the present disclosure. Functional categorization of these genes was determined by pathways the genes were involved in.

These dispersed R-ELEMENT sequences on pathogen genomes may be used as targets to debilitate pathogen genome as well as flanking genes (which include virulence and survival genes, in this case) simultaneously at distant multiple locations and carrying out changes like but not limited to gene silencing, gene recombination, gene substitution with a new function etc.

The R-ELEMENTS are tested for the presence of potential secondary structures formation. Accordingly two methods may be used to target R-ELEMENTS described hereafter. Case I: If R-ELEMENT is found to be palindromic the following three strategies may be used.

Strategy I includes use of R-ELEMENT as target and inserting a strong palindromic sequence to ensure the down-regulation of transcription of flanking genes (Palindromic sequences in a transcription bubble form hairpin loops which hinders DNA transcription by stalling the RNA polymerase enzyme thereby down-regulating the expressions of the flanking gene).

Strategy II includes use of R-ELEMENT as target to nick the pathogen genome at multiple locations and cleave the flanking genes (Hairpin loops formed in the mRNA could be involved in prevention of the early decay of mRNA thereby promoting the expression of important bacteria genes.

Strategy III is utilized if R-ELEMENT is followed by a poly-A tail indicative of a transcription terminator. If the R-ELEMENT is found to be a terminator, the R-ELEMENT is used as target and a strong palindromic sequence is inserted to ensure that the transcriptional termination of the flanking genes occur and these genes are down-regulated in the pathogen.

In Case II: If R-ELEMENT is not found to be palindromic, the R-ELEMENT is used as target to nick the pathogen genome at multiple locations and cleave the flanking genes.

In the present embodiment, the R-ELEMENT sequence is used as an example. If the R-ELEMENT is palindrome and is shown to inhibit flanking genes by stalling RNA polymerase: R-ELEMENT can be used as a target and a strong palindromic sequence is inserted to ensure the down-regulation of transcription of flanking genes. Palindromic sequences in a transcription bubble form hairpin loops which hinders DNA transcription by stalling the RNA polymerase enzyme thereby down-regulating the flanking gene expression.

If the R-ELEMENT is a palindrome and is shown to promote flanking genes by increasing mRNA stability: R-ELEMENT can be used as target to nick the pathogen genome at multiple locations and the flanking genes are cleaved. Hairpin loops formed in the mRNA could be involved in prevention of the early decay of mRNA, and cleaving these sequences impedes the expression of the flanking genes.

It should be appreciated by those skilled in the art that any block diagram herein represents conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

According to an embodiment of the disclosure, the sample is collected from the infected area using the sample collection module 104. In this module, the method utilized for extracting samples from the infected sites depends largely on the site of infection. In an embodiment, in cases of topical infection in a living organism (e.g., skin infections caused by *Staphylococcus epidermidis* etc.). The collected sample from the infected is one or more of fecal matter, blood, urine, tissue biopsy, hospital surfaces or environmental samples. Various techniques are used as per the guidance of the physician such as a sterile swab (for example, cotton swabs) for sample collection from the mucosal lining and saliva, a sterile syringe for sample collection from the pus and aspirations of fluids. A skin scrape can also be performed for sample collection from the infected sites on the skin. Also, tissue biopsy can be performed in order to obtain the samples.

In an embodiment where the site of infection is an internal organ such as lung, gut etc. different techniques are employed based on the organ from which the sample is being collected. In one embodiment, where the infection is in lung (for example, infection caused by *Mycobacterium tuberculosis, Pseudomonas aeruginosa*, etc.), sample collection from the fluids in the lung due to the infection could be done by one of the following methods such as broncho-alveolar lavage collection, bronchial brushings, endobronchial biopsies and nasal scrape etc. In yet another embodiment, in case of infection in the upper respiratory tract sample collection from lung can be performed by oropharyngeal (OP) and nasopharyngeal (NP) swabs and sputum collection. In another embodiment where site of infection is the gut (for example, infection caused by *Klebsiella pneumoniae*), fecal samples are collected to identify the pathogen infecting the gut. Samples may be collected using Endoscopic biopsy of gastrointestinal tract in cases where the infection does not present in the fecal sample. In another embodiment where the site of infection in any other major organ such as liver, heart, kidney, etc. the sample may be collected through needle biopsy at the site of infection. In case where the site of infection is in brain tissue sample collection may be performed via CT (Computed Tomography) guided aspiration, a type of needle biopsy.

In yet another embodiment, in case of blood borne pathogens such as *Staphylococcus aureus* and *Pseudomonas aeruginosa*, the sample can be extracted through collection of blood components. Acute serum collected from the patients (containing high concentration of infectious bacteria) can be used. Additionally, the whole blood sample can be submitted for bacterial culturing or the whole blood plasma can be utilized for further procedure. In yet another embodiment, samples can also be collected from urine in cases where the there is an infection of urinary tract or in some cases the infection of gut.

In an embodiment where the site of infection is in plants (e.g., citrus cranker caused by *Xanthomonas axonopodis*), samples can be obtained from the whole plant or plant parts such as root, stem, leaf, seeds, fruits, etc. Using a whole plant for sample collection may be better suited to identify the pathogen unless it is clearly known that the disease affects only a particular part. Soil samples within the top 10 cm of the root zone in and around the infected root of the plant can also be collected to identify the disease pathogen.

In another embodiment, the site of infection can also be an environment such as soil, air, water or surfaces (such as infection of *Staphylococcus aureus* and *Pseudomonas aeruginosa* in hospital surfaces), etc. Sample collection from a surface can be performed through the use of sterile swab. Dry swabs may be recommended for wet surfaces and wet swabs may be recommended for dry surfaces. Swabbing of the test surface may be performed by rolling the swab lightly back and forth. Water and soil samples can be collected from the environmental site of infection and sent for further procedure. Air samples can also be collected to identify the presence of air borne pathogen. Volumetric air samples for culture analyses can be taken by impacting a known volume of air onto a suitable growth medium. Any other laboratory accepted method of sample extraction/collection from environment as well as living organisms is within the scope of this invention.

It should be appreciated, that the bacterial cells are isolated from the extracted sample before being presented to the pathogen detection and DNA extraction module 106 in cases where the pathogen is known to be culturable. In case of non-culturable pathogen, the collected samples are directly processed to the pathogen detection and DNA extraction module 106, DNA/RNA is isolated and extracted from the sample using laboratory standardized protocols using the pathogen detection and DNA extraction module 106 and sequencing is performed using the sequencer 108. The nucleotide sequences obtained after sequencing of extracted DNA/RNA sequences are then provided to the processor 112 using the user interface 102. The nucleotide sequences can be obtained for 16S rRNA, a nucleotide sequence encoding for any particular gene of interest being amplified, or sequences of DNA fragments corresponding to whole genome sequencing or shotgun sequencing. In one embodiment, DNA/RNA can be extracted using a DNA isolation and extraction isolation kits such as miniprep and other methods standardized in laboratory setups. The extracted DNA is then provided into the sequencer 108 and the sequences so obtained are fed into the processor 112 using the user interface 102. The user interface 102 is operated by a user. The user interface 102 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite.

The pathogen detection and DNA extraction module 106 is also configured to utilize experimental techniques to detect pathogens present in an infected site. The use of any laboratory acceptable methods of detecting presence of pathogens present at the infected site is within scope of the disclosure. In one embodiment, presence of viable living cells can be detected by utilizing presence of bacterial mRNA which has a short half-life and will not exist once the cells are dead. This mRNA based method may involve identifying antigen/protein specific for the pathogen which can be utilized as a marker for that pathogen and produced by the pathogen in abundance and the corresponding gene on the pathogen genome can be obtained (e.g. A and B toxins in *Clostridium*, Staphylococcal enterotoxin A and Hemolytic toxin in *Staphylococcus aureus*, alpha antigen for *Mycobacterium tuberculosis* etc). The mRNA corresponding to expression of these genes can be detected using techniques like but not limited to polymerase chain reaction (RT-PCR) assays or reverse transcriptase strand displacement amplification (RT-SDA) assays. In another embodiment, expression of proteins identified as specific to these pathogens can be detected using various laboratory accepted methods for protein purification and detection (toxins A and B produced by *Clostridium*, toxins-antitoxin systems in *Mycobacterium tuberculosis* etc.). Chromogenic enzyme assays for a pathogen are also within scope of the invention. Specific metabolites or compounds produced by a pathogen can also be detected (using different laboratory acceptable methods like Mass spectrometry, HPLC-MS, spectrometry-based methods etc.) to ascertain pathogen presence (e.g. Phenazine production in *Pseudomonas aeruginosa*). In other embodiments, the identified antigens/marker sequences (e.g. sequence-characterized amplified region (SCAR) markers in *Xanthomonas axonopodis*) can be targeted using methods like nucleic acid amplification tests (NAAT), real time PCR, immunoassays etc. as well as specific staining and microscopy techniques and flow cytometry methods of detecting pathogens are also within scope of this invention. PCR or Restriction Fragment Length Polymorphism (RFLP) based detection of 16S rRNA in order to identify pathogens can also be utilized. In one more embodiment, staining methods can also be utilized to identify a pathogen and establish viability of a pathogen cell (e.g. propidium iodide can be used for identifying dead cells). Cell toxicity assays can also be utilized for toxins based detection of pathogens. Further in case of sporulating bacteria, spore detection assays can also be utilized. In case of culturable bacteria, the viability of pathogens can even be established by culturing methods using selective media followed by methods to detect specific pathogens discussed above. In case of an infection in living beings observation of phenotypic effects like alleviation of infection symptoms is also within scope of this disclosure. The symptoms may vary with type of infection and may be observed by registered medical practitioner or healthcare professional. Any other method of detecting pathogens are also within scope of this disclosure.

According to an embodiment of the disclosure, the DNA extraction module 106 is configured to applying one or more techniques for identification or detection of microbes in a collected sample comprising a sequencing technique, a flow cytometry based methodology, a microscopic examination of the microbes in collected sample, microbial culture of pathogens in vitro, immunoassays, cell toxicity assay, enzymatic, colorimetric or fluorescence assays, assays involving spectroscopic/spectrometric/chromatographic identification and screening of signals from complex microbial populations, The pathogen or microbial characterization data may comprise one or more of sequenced microbial DNA data, a Microscopic imaging data, a Flow cytometry cellular measurement data, a colony count and cellular phenotypic data of microbes grown in in-vitro cultures, immunological data, proteomic/metabolomics data, and a signal intensity data. The sequenced microbial data obtained from the sequencer 108 comprises one or more of sequences obtained from next generation sequencing platforms corresponding to marker genes including 16S rRNA, Whole Genome Shotgun (WGS) sequencing, a fragment library based sequences, a mate-pair library or a paired-end library based sequences, or a combination thereof. The sequencing data may also comprise of complete genome sequences of the pathogens obtained within a collected sample. In one embodiment, the taxonomic groups or pathogens within a sample collected can be obtained by amplification of marker genes like 16S rRNA within bacteria. In another embodiment, the taxonomic groups or pathogens within a sample can be obtained by the binning of whole genome sequencing reads into various taxonomic groups using different methods including sequence similarities as well as several methods using supervised and unsupervised classifiers for taxonomic binning of metagenomics sequences.

According to an embodiment of the disclosure, the processor 112 comprises the nucleotide repeat sequence identification module 114. The nucleotide repeat sequence identification module 114 is configured to identify a set of nucleotide repeat sequences in the extracted DNA which occur more than a predefined number of times in the genome and are dispersed at distant locations on the genome. The predefined number refers to the number of occurrences of nucleotide repeat sequence on genomic sequences of all pathogenic strains of candidate pathogens in a dispersed manner and this number might vary with system and pathogen under consideration. A minimum of 10 occurrences dispersed at distant locations on the genome of the pathogen is required for a nucleotide repeat sequence to be considered. Further, it is important to ensure that the identified nucleotide repeat sequence region is specifically present on the genomes of a particular pathogenic genus only and on nucleotide based sequence alignment does not show more than two cross matches with other genera or commensals within the pathogenic genus/species. Cross match refers to the occurrence of identified repeat sequence region more than two times in a genus which is different from the candidate genus in which the repeat sequence has been identified as is to be used as a target site. Following method can be used for the identification of the nucleotide repeat sequence region on a genome.

Figure 2A:
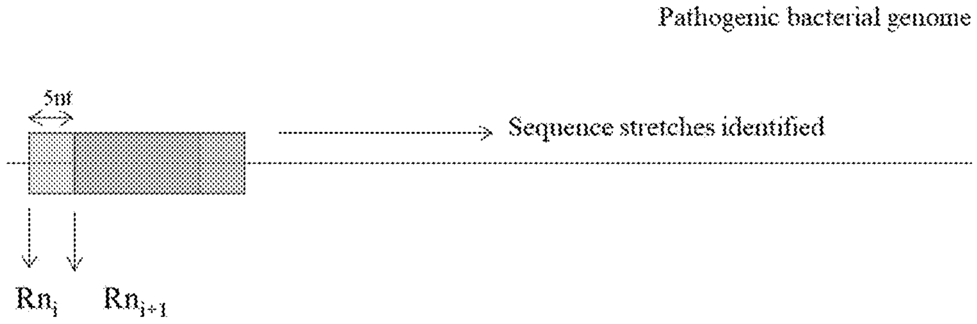
FIG. 2A illustrates a schematic representation of the method through which nucleotide repeat sequences are identified according to an embodiment of the disclosure.
Figure 2B:
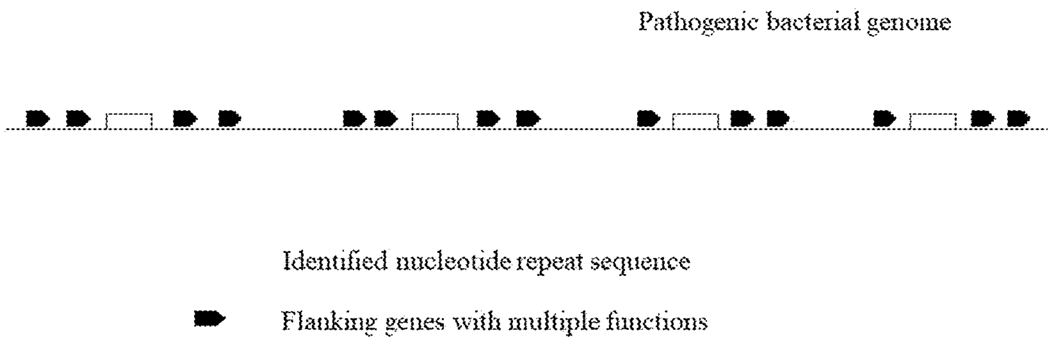
FIG. 2B illustrates occurrence of nucleotide repeat sequences in a pathogen genome according to an embodiment of the disclosure.

Initially, sequence stretches Rn of predefined length are picked keeping the difference in the start position of consecutive picked nucleotide stretches Rni+1 and Rni as 5 nucleotide (might vary depending upon the system) as shown in FIG. 2. Predefined length Rn refers to the length of a stretch of nucleotide sequence picked from the genome sequence of candidate pathogen or different strains of candidate pathogen) used as a seed input for local sequence alignment tools. This predefined length may differ depending on the pathogen and vary between 10 to 60 nucleotides. In the next step, a reference genome based nucleotide sequence alignment tool is applied in order to align the picked nucleotide sequence stretch with nucleotide sequences corresponding to genomes of all pathogenic strains belonging to the candidate pathogen, genus or species. In an example, PILER has been used for the alignment, though use of any other method or any other tool is well within the scope of this disclosure. Sequence based search utilizing any other sequence alignment or nucleotide repeat finding tools are also within scope of this invention. A relaxation of two mismatches for local alignment can be allowed but may vary with the system and allowed to prevent false positives which could lead to over-prediction of possible targets. In the next step, if the number of times Rn matches on the genome is greater than the predefined threshold, the sequence stretch is termed as an R-ELEMENT. The R-ELEMENT can be palindromic or non-palindromic in nature. Depending on the type of the R-ELEMENT a methodology may be identified to treat the pathogenic infection as described in the previous part of the disclosure. Although, the number of occurrences of the nucleotide repeat sequence might vary in different pathogens, a minimum of 10 occurrences is required for a nucleotide repeat sequence to be considered as a target sequence The dispersed nucleotide sequences at distant locations on the genome refers to stretches of nucleotide sequences which occur across the genome with a distance of predefined number of base pairs between them In one embodiment used in this disclosure the predefined number refers to a separation of >10000 base pairs between two nucleotide repeat sequences. If the number of times Rn matches on the genomic sequences of strains of candidate pathogen genome/genomes is greater than the predefined threshold with a minimum value of 10, the sequence stretch is termed as target nucleotide repeat sequence. The nucleotide repeat sequences which are conserved across all genome sequences corresponding to strains of a candidate pathogen or genus would indicate the said conserved sites. Any other method of identification of conserved sites is also within the scope of this disclosure.

According to an embodiment of the disclosure, the processor 112 includes the neighborhood gene identification module 116. The neighborhood gene identification module 116 is configured to identify a set of neighborhood genes present upstream and downstream of the set of the nucleotide repeat sequences on the genome of the candidate pathogen. In the present example the set of neighborhood genes are the neighborhood of identified R-ELEMENTS. On each genome G of Genus $G_e$ where R-ELEMENT or its reverse complement occurs, flanking genes are identified on either side and on each strand of Genome G. In an embodiment, 10 genes are included but the span may vary with each system.

According to an embodiment of the disclosure, the system 100 further includes the annotation module 118. The annotation module 118 categorizes or annotates the set of neighborhood genes on the pathogen genomes based on their functional roles in the pathogen. Functional annotation of the set of neighborhood genes is performed using HMM search. The use of any other methods such as PSSM, BLAST etc. is well within the scope of the disclosure. These R-ELEMENT sequences can be used as targets which can be further extended to target multiple flanking genes (which includes virulence and survival genes) simultaneously and carry out changes like but not limited to gene silencing, gene recombination, gene substitution with a new function etc.

According to an embodiment of the disclosure, the system 100 further includes the testing module 120 and the administration module 122. The testing module 120 is configured to check the presence of secondary structure formation in the identified set of nucleotide repeat sequences. There could be the presence of the secondary structures such as hairpin loop formation. Depending on the presence of the secondary structure, the administration module 122 is configured to administer an engineered polynucleotide construct to treat the pathogenic infection, wherein the engineered polynucleotide construct is comprising: one or more of the set of nucleotide repeat sequences occurring in multiple copies at dispersed locations on the candidate pathogen genomes, a first enzyme capable of nicking and cleaving the identified set of nucleotide sequences, and a second enzyme capable of removal of a set of neighborhood genes flanking the set of nucleotide repeat sequences. wherein the engineered polynucleotide construct is comprising: one or more of the nucleotide repeat sequences RELEMENT with multiple copies at dispersed locations on the candidate pathogen genomes of one or more of the pathogenic strains of candidate pathogen genus or species, a first enzyme capable of nicking and cleaving the identified set of nucleotide sequences, and a second enzyme capable of removal of a set of neighborhood genes flanking the set of nucleotide repeat sequences. The engineered polynucleotide construct works in such a way that it targets multiple regions in the genome simultaneously.

In an embodiment the engineered polynucleotide construct may comprise of an engineered circular DNA comprising of an origin of replication. Further the engineered polynucleotide construct may comprise of regulatory elements including a promoter sequence, ribosomal binding site, start codon, a cassette comprising of first and second enzyme flanking the nucleotide repeat sequence or the reverse complement of the nucleotide repeat sequence R-ELEMENT cloned into the system, stop codons and transcription terminator. The promoter sequence may depend on the pathogen being targeted as well as the regulation required to express the components of the engineered polynucleotide construct at a specific targeted site (for example, within a living being or an infected area). The engineered polynucleotide construct may also be equipped to create a poly A tail in mRNA to stabilize the sequence. The poly A tail refers to a stretch of polynucleotide Adenine nucleotides at the 3' end of mRNA. In one embodiment, the first and second enzyme can be nickase and exonuclease cloned in any order. The target R-ELEMENT within the candidate pathogen genome can be recognized and bound by the reverse complement sequence and the complex thus formed can be nicked by the nickase enzyme. The exonuclease can then cut the duplex formed as well as flanking genes once it recognizes a nick. In another embodiment, the enzymes can be cas9 sequences (may be obtained from *Streptococcus pyogenes*) flanking the R-ELEMENT or the reverse complement of R-ELEMENT which can both act as sgRNA (single guide RNA) for the obtained CRISPR-Cas (Clustered Regularly Interspaced Short Palindromic Repeats) system. The reverse complement of target nucleotide repeat sequence is obtained by interchanging letters A and T and interchanging letters C and G between target and complement sequences. The reverse complement refers to the sequence corresponding to the identified nucleotide repeat sequence in the opposite strand of DNA. The R-ELEMENT or its reverse complement is recognized by the reverse complement sequence or the target R-ELEMENT sequence on the polynucleotide construct and the complex formed by the binding of R-ELEMENT sequence to its reverse complement. The cas9 may then act as an endonuclease and cut the nick and flanking sequences. The nucleotide repeat sequence can be targeted by delivering an engineered polynucleotide construct using a bacterial, plasmid or a viral vector to the target bacterial cell. In one embodiment the composition may comprise of: the first element comprising a polynucleotide sequence of CRISPR-Cas system wherein the polynucleotide sequence may comprise a nucleotide sequence (identified repeat or its reverse complement) called a guide sequence capable of hybridizing to target sequence (nucleotide repeat sequence on pathogen), a tracr sequence and a tracr mate sequence. The second element may comprise of CRISPR enzyme coding sequences like CAS enzymes. It should be noted that in all these embodiments multiple RELEMENT sequences can be cloned within same polynucleotide sequence along with a bacterial or viral vector and the other features mentioned above to target more than one pathogen using the same compact construct. Any other construct cassette that may bring about the recognition of the RELEMENT sequences in genomes of bacterial and subsequent nicking and cutting of RELEMENT sequences and the flanking genes is within the scope of this invention.

In another embodiment, in addition to the above mentioned features, if bacterial conjugation is to be used as a construct delivery method, the engineered polynucleotide construct may comprise of a relaxase, coding sequences for structural proteins (e.g. pili) and those for regulatory proteins for conjugation. It should be noted that in both embodiments multiple R-ELEMENT sequences can be cloned to target more than one pathogen using the same compact construct. Any other construct cassette that may bring about the recognition of the R-ELEMENT and subsequent cutting of R-ELEMENT and the flanking genes is within the scope of this invention. These polynucleotides comprising the nucleotide repeat sequence, the genes encoding enzymes and the other features discussed above can be inserted into laboratory acceptable vectors which allow insertion of external DNA fragments; In one embodiment construct may be carried by vectors like plasmid or phage based cloning vectors. The regulatory elements can be designed according to information available for the pathogen being targeted.

The administration module 122 is configured to administer a construct to treat the pathogenic infection. The administration module 122 can use any pharmaceutically acceptable method of carrying the engineered polynucleotide construct to target the conserved nucleotide sequences in a pathogen genome. In different embodiments the utility can be, but not limited to oral medicine, topical creams, nasal administration, aerosol sprays, injectable cocktail etc.

In an embodiment, the engineered polynucleotide construct can be administered to the infected site (either living beings or environmental site) through targeted construct delivery methods such as the use of targeted liposomes wherein, the liposome is tagged on the external surface with molecules that may be specific and functionally important to the candidate genus and the tagged liposome can be used to transfer the engineered polynucleotide construct into the pathogen), targeted nanoparticles wherein, a targeting molecule that is specific to the candidate genus can be attached to the nanoparticle (like but not limited to Ag or Au nanoparticle) along with the engineered polynucleotide construct, thereby allowing the tagged nanoparticle to release the engineered polynucleotide construct into the pathogen, phage based delivery method (wherein, the engineered polynucleotide construct can be placed within the phage infecting the candidate genus thereby transferring the engineered polynucleotide construct into pathogen) and bacterial conjugation (wherein, the engineered polynucleotide construct can be placed in other bacteria that can conjugate with the candidate genus and the engineered polynucleotide construct can be transferred to the pathogen through natural conjugation method) etc. In an embodiment, the lipid constitution of the membrane for the targeted liposome can be modified to target specific set of bacteria. In one example, liposomes containing lipids like Dipalmitoyl phosphatidyl Choline (DPPC) and cholesterol can lead to release of the engineered polynucleotide construct within contained the liposome after encountering rhamnolipids which are prevalent in *Pseudomonas aeruginosa* biofilms. Similarly, cationic liposomes with lipid constitution comprising dioctadecyldimethylammonium bromide (DDAB) may be used to target *Staphylococcus* biofilms. In another example, *Staphylococcus aureus* biofilms are targeted by utilizing antigens like Wheat Germ agglutinin as ligands on nanoparticles to specifically penetrate and bind to *S. aureus*. In another embodiment, immunoliposomes can be created with specific antibodies towards ligands of specific pathogen (for example, antibodies against concanavalin A for targeting extracellular matrix of biofilms). The lipid bilayer can be made sensitive to the toxins or other virulence factors of the pathogen in order to release the engineered polynucleotide construct only in infected areas where toxins are present. In another embodiment, the engineered polynucleotide construct can be adsorbed or covalently linked to heavy metals (called gene guns or micro-projectiles) and carried to targeted pathogen bacterial cell.

In another embodiment, the engineered polynucleotide construct can also be administered to the infected site through non-targeted construct delivery methods such as the use of non-targeted nanoparticles (wherein, nanoparticles can form cages that can hold the engineered polynucleotide construct which are then released into the pathogen), non-targeted liposomes (wherein, the liposomes are phospholipid capsules which can be used to hold the engineered polynucleotide construct that can then merge with the pathogen cell membrane to release the engineered polynucleotide construct inside the pathogen) etc. In an embodiment, attenuated bacteria can also be used to deliver nanoparticles into tissue spaces where they can be released to act upon actual site of infection (as shown in creation of Nano-BEADS in a study where *Salmonella* was used to deliver nanoparticles containing a drug to deep tissues). In another example, minicells produced by bacteria can also be used to package the engineered polynucleotide construct and deliver it to specific areas in the infected site. In another embodiment, these delivery methods can be used to target the engineered polynucleotide construct to infected surfaces also. Any other laboratory accepted method of administration of the engineered polynucleotide construct to the infected site is within the scope of this disclosure.

According to an embodiment of the disclosure, the efficacy module 124 is used to assess the efficacy of the treatment methodology described in this disclosure. The efficacy module 124 comprises of any laboratory acceptable methods of detecting presence of pathogens present at the infected site. In one embodiment, presence of viable living cells can be detected by utilizing presence of bacterial mRNA which has a short half life and will not exist once the cells are dead. This mRNA based method may involve identifying antigen/protein specific for the pathogen which can be utilized as a marker for that pathogen and produced by the pathogen in abundance and the corresponding gene on the pathogen genome can be obtained (for e.g. A and B toxins in *Clostridium*, Staphylococcal enterotoxin A, leukocidin and Hemolytic toxin in *Staphylococcus aureus*, alpha antigen for *Mycobacterium tuberculosis* etc). The mRNA corresponding to expression of these genes can be detected using techniques like but not limited to polymerase chain reaction (RT-PCR) assays or reverse transcriptase strand displacement amplification (RT-SDA) assays. In another embodiment, expression of proteins identified as specific to these pathogens can be detected using various laboratory accepted methods for protein purification and detection (toxins A and B produced by *Clostridium*, toxin-antitoxin in *Mycobacterium tuberculosis* etc.). Chromogenic enzyme assays for a pathogen are also within scope of the invention. Specific metabolites or compounds produced by a pathogen can also be detected (using different laboratory acceptable methods like Mass spectrometry, HPLC-MS, spectrometry-based methods etc.) to ascertain pathogen presence (e.g. Phenazine production in *Pseudomonas aeruginosa*). In other embodiments, the identified antigens/marker sequences (e.g. sequence-characterized amplified region (SCAR) markers in

*Xanthomonas axonopodis*) can be targeted using methods like nucleic acid amplification tests (NAAT), real time PCR, immunoassays etc. as well as specific staining and microscopy techniques and flow cytometry methods of detecting pathogens are also within scope of this invention. PCR or Restriction Fragment Length Polymorphism (RFLP) based detection of 16S rRNA in order to identify pathogens can also be utilized. In one more embodiment, staining methods can also be utilized to identify a pathogen and establish viability of a pathogen cell (e.g. propidium iodide can be used for identifying dead cells). Cell toxicity assays can also be utilized for toxins based detection of pathogens. Further in case of sporulating bacteria, spore detection assays can also be utilized. In case of culturable bacteria, the viability of pathogens can even be established using culturing methods based on selective media followed by methods to detect specific pathogens discussed above. In case of an infection in living beings observation of phenotypic effects like alleviation of infection symptoms is also within scope of this disclosure. The symptoms may vary with type of infection and may be observed by registered medical practitioner or healthcare professional. Any other method of detecting pathogens are also within scope of this disclosure. In case pathogen presence is detected, the engineered polynucleotide construct can be administered again using administration module 120 and repeated till pathogen is eliminated.

In operation, a flowchart 200 illustrating the steps involved for treating the pathogenic infection in the genome is shown in FIG. 3A-3B. At 202, a sample is obtained from an area infected from the pathogen. At step 204, DNA is extracted from the sample using the pathogen detection and DNA extraction module 106. At step 206, the extracted DNA is sequenced using the sequencer 108. At step 208, the pathogen is detected from the obtained sample. At step 210, a set of nucleotide repeat sequences in the extracted DNA is identified which occur more than a predefined number of times in the pathogen genome where minimum value of predefined number is 10. The identified set of nucleotide repeat sequences correspond to R-ELEMENT in the pathogen genome. The R-ELEMENTS are tested for secondary structure formation. Accordingly different strategies are used. At step 212, a set of neighborhood genes present upstream and downstream of the set of nucleotide repeat sequences is identified.

Further at step 214, the each of the identified set of neighborhood genes is categorized according to functional roles of each of neighborhood gene in the pathogen. The number of neighborhood genes can be decided by a user. At step 216, the presence of a secondary structure is tested in the identified set of nucleotide sequence.

Figure 4:
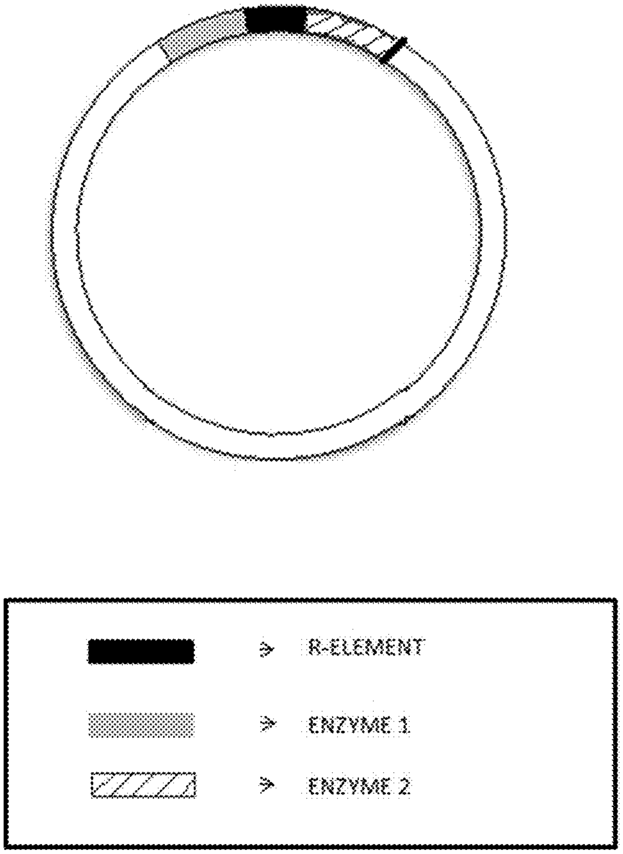
FIG. 4 shows schematic representation of a construct for targeting identified nucleotide sites in a pathogen according to an embodiment of the disclosure.

At step 218, an engineered polynucleotide construct is administered on the infected area to combat the infections due to the pathogens, wherein the engineered polynucleotide construct is comprising:

- one or more of the set of nucleotide repeat sequences of multiple copies dispersed in nucleotide sequences of genomes,
- a first enzyme capable of nicking and cleaving the identified set of nucleotide sequences, and
- a second enzyme capable of removal of a set of neighborhood genes flanking the set of target nucleotide repeat sequences;

The administration of construct aims at targeting the set of nucleotide sequences and removal of flanking genes on genomes of pathogen infecting the area. The engineered polynucleotide construct works in such a way that it targets multiple regions in the pathogenic genome simultaneously. The prototype of the engineered polynucleotide construct for targeting identified nucleotide sites in a pathogen is depicted in FIG. 4. At step 220, the efficacy of the administration module 122 is assessed and in case pathogen presence is detected at the site, the administration module 122 can be utilized repetitively till pathogen is eliminated from the site. And finally, at step 222, the engineered polynucleotide construct is re-administered if the pathogen is still present after checking using efficacy module 124 in the infected area.

Figure 5:
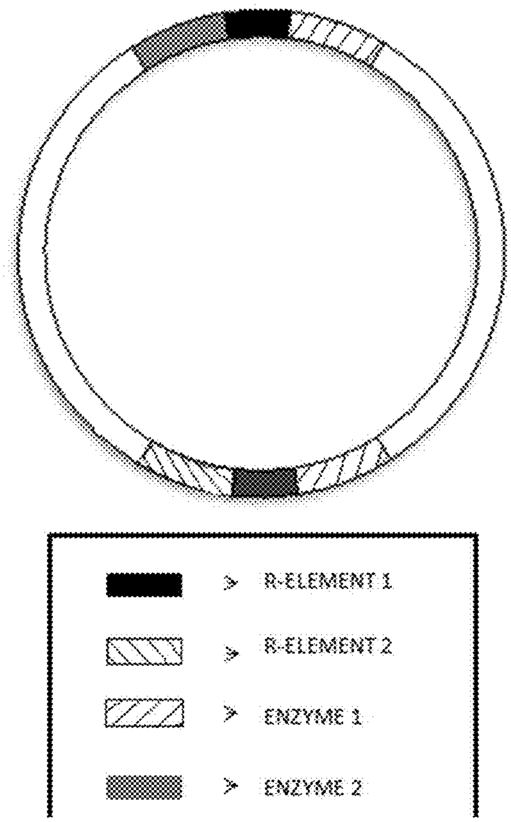
FIG. 5 depicts the engineered polynucleotide construct for targeting identified nucleotide sites on multiple pathogens simultaneously according to an embodiment of the present disclosure.

In another embodiment, the method described in this disclosure may be used to identify R-ELEMENT in multiple pathogens identified in the collected sample using the one or more criteria as discussed in the above paragraphs. A construct may be created by including each of the identified R-ELEMENTS corresponding to each of the pathogens identified within the collected sample and the enzymatic machinery capable of targeting the matched complementary sequences and flanking genes. Such construct may be utilized to target multiple pathogens in an infected area simultaneously (Prototype of construct is depicted in FIG. 5).

In another embodiment, literature mining and manual curation was utilized to catalogue or create a knowledgebase of antibiotic resistant pathogens as well as the corresponding R-ELEMENTS identified using the methodology described in the present disclosure. The pathogens within the catalogue may be categorized on the basis of the environments the pathogens inhabit. The catalogue (termed as RCAT) may be utilized to prepare the engineered polynucleotide constructs including multiple R-ELEMENTS corresponding to multiple pathogens infecting the environment from which a sample is obtained or for multiple pathogens whose elimination is desired in an infected area. The engineered polynucleotide constructs may then be used to target multiple pathogens simultaneously in order to combat an infection as shown in FIG. 5.

According to an embodiment of the disclosure, the system 100 can also be used in combination with various other known methods to effectively treat the pathogenic infection. In an example, the method 200 can be used as preventive method. The method can be used in combination with various other antibacterial agents. One implementation would be the use of quorum quenchers along with the engineered polynucleotide construct to tackle the biofilm formation in hospital surfaces. In another example, the method may be used as a therapeutic measure. The method may be used in combination with various other antimicrobial methods. One implementation would be to use the method along with antibiotics and vaccines against essential proteins for therapeutic purposes.

Figure 6:
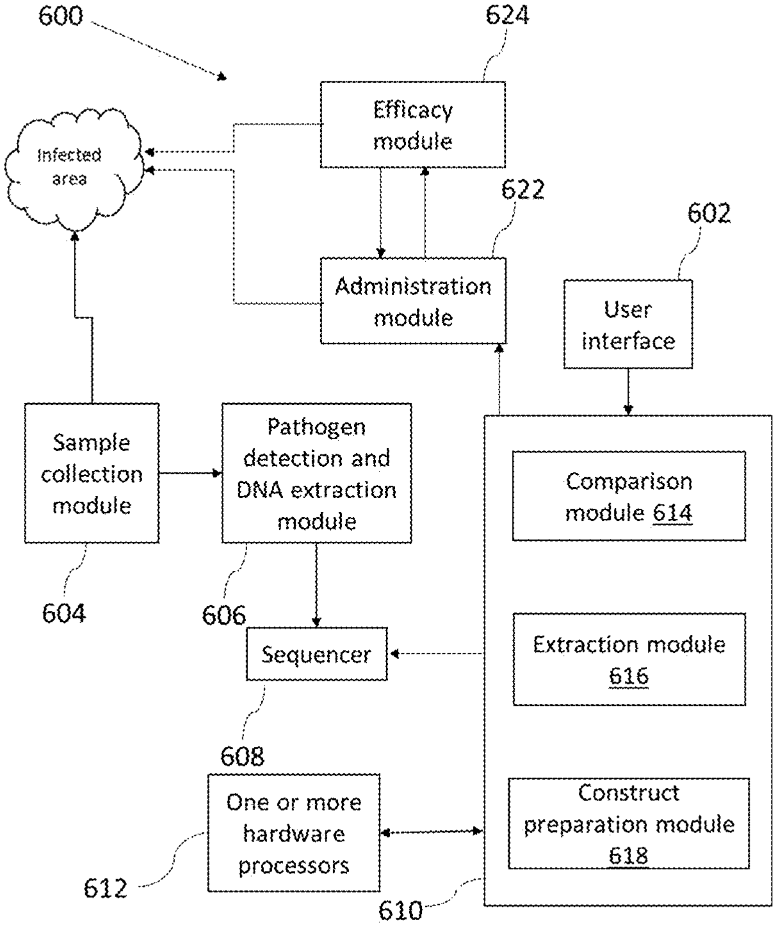
FIG. 6 illustrates a block diagram of a system for identification of target sites in a non-culturable sample to treat a pathogenic infection according to an embodiment of the present disclosure.
Figure 7:
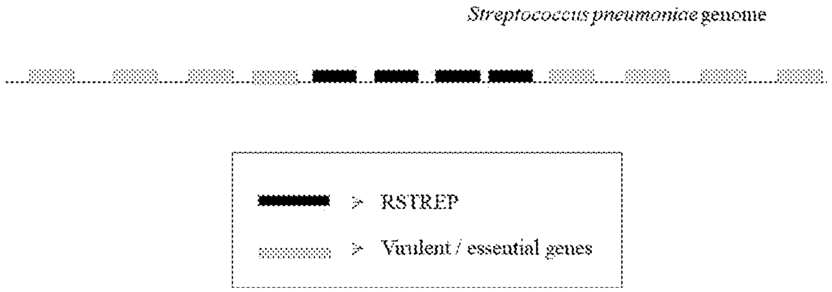
FIG. 7 depicts a schematic representation of *Streptococcus pneumoniae* genome showing RSTREP element according to an embodiment of the disclosure.
Figure 8:
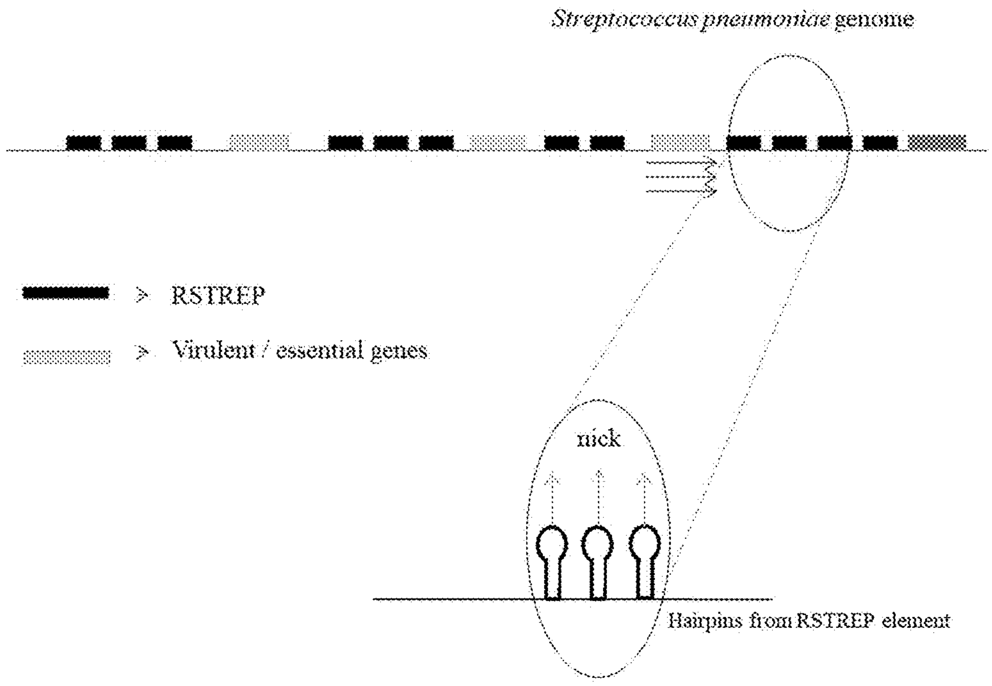
FIG. 8 depicts a schematic representation of *Streptococcus pneumoniae* genome showing the method of targeting of the repeated palindromic nucleotide sequence.
Figure 9:
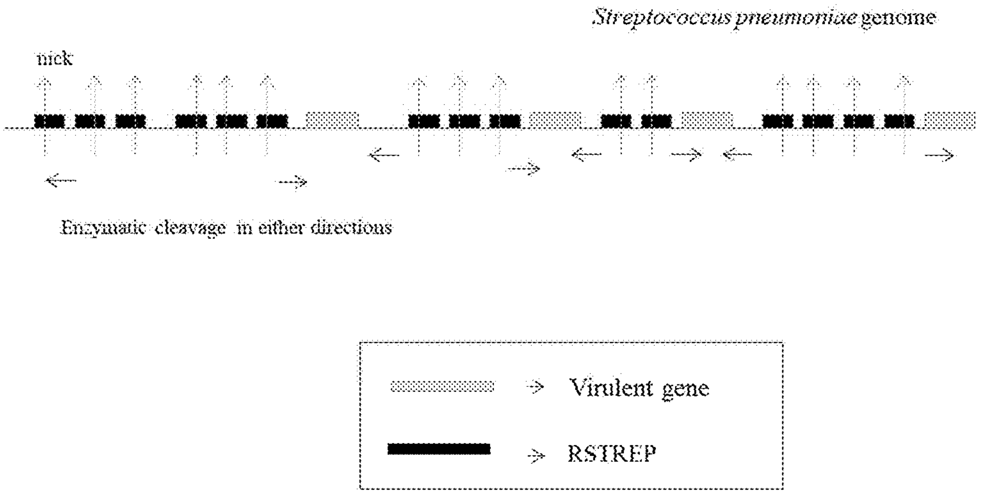
FIG. 9 depicts a schematic representation of *Streptococcus pneumoniae* showing enzymatic cleavage in either directions according to an embodiment of the disclosure.

In another embodiment, as shown in FIG. 6, a system, namely, system 600 is used in combination with various other known methods to effectively treat the pathogenic infection. The system 600 is configured to identify the target sites in a non-culturable sample to treat the pathogenic infection. The non-culturable sample contains pathogens that cannot be grown in a laboratory settings because the ideal conditions and media for their growth is not well characterized. Such pathogens can be identified and treated via the system 600 described in the present embodiment. The system 600 includes a memory 610 and a processor 612. The processor 612 is in communication with the memory 610 via a user interface 602. Herein the sample is obtained from an infected area through a sample collection module 604 and is subjected to DNA isolation and extraction using standardized methods through a pathogen detection and DNA extraction module 606. The pathogen detection and DNA extraction module 606 is further configured for detection of pathogens similar to module 106 in system 100. The obtained DNA is sequenced using a sequencer 608. Reads obtained from the sequencer 608 is provided to processor 612 using the user interface 602. Though the system 600 is different embodiment of system 100, the functional aspect and operation of the memory 610, processor 612, user interface 602, sample collection module 604, the DNA extraction module 606 and the sequencer 608 in system 600 are same as the memory 110, processor 112, the user interface 102, the sample collection module 104, the DNA extraction module 106 and the sequencer 108 in system 100 respectively. The processor 612 further includes a plurality of modules for performing various functions. The processor 612 comprises a comparison module 614, an extraction module 616 and a construct preparation module 618. The comparison module 612 is configured to compare the reads obtained after sequencing to the R-ELEMENT repository RCAT in order to identify pathogens within the sample. The extraction module 616 is configured to extract the R-ELEMENT corresponding to each of the pathogen from RCAT to be used as targets against the identified pathogens. And the engineered polynucleotide construct preparation module 618 is configured to prepare the engineered polynucleotide construct comprising the R-ELEMENTS to which matches are obtained in the sample and the enzymatic machinery capable of targeting the matched complementary sequences and flanking genes in order to debilitate multiple pathogens simultaneously in the infected area. The prepared construct is administered to the infected area through an administration module 622. Further an efficacy module 624 is utilized to assess the efficacy of the administration module 622 in elimination of pathogen. The efficacy module 624 is similar to module 124 in system 100. In case presence of pathogen is detected, administration module can be applied followed by efficacy module 624 repetitively until pathogen is completely cleared. In another embodiment, the R-ELEMENT repository RCAT may be used to create probes for each pathogen. RELEMENT corresponding to a pathogen may be utilized as a probe to detect presence of the pathogen in an infected area or a given sample. The use of any accepted multitude of signal detection methods (e.g. fluorophores, chemical detection methods etc.) is within the scope of this invention According to an embodiment of the disclosure, the system and method may also be explained with the help of an example of *Streptococcus pneumonia* as shown in FIG. 7-FIG. 9. *Streptococcus pneumoniae* is a gram-positive bacteria that occurs in the upper respiratory tract of humans which can cause pneumonia in infected patients when conditions are conducive. Pneumonia is the inflammation of lung, affecting primarily the air sacs and in rare cases, *Streptococcus pneumoniae* can also cause pneumococcal meningitis and sepsis.

The set of nucleotide sequences were identified which were repeated on *Streptococcus pneumoniae* genome by taking a sequence stretch Rn of predefined length (30-60 in this case) and searching across the genome for similar sequence stretches by any alignment software. In this embodiment, software PILER was used. The following consensus sequence is found to be repeated in Sequence 001: *Streptococcus pneumonia* genome:

G[CT]AT[AC]N[AT][AG]TCA[AG]GN$_{(4,15)}$[CT]TT-GATNN[TG]AT[AG]C

The genes surrounding the identified nucleotide sequence repeat and its reverse complement were obtained. The conserved stretches (as shown above) are found in the vicinity of highly virulent and, certain essential genes of *S. pneumoniae* (as shown in Table 1) and are found dispersed across distant genomic locations in *Streptococcus pneumoniae* genome. Results of sequence similarity analysis (using BLAST in this particular example) revealed that this sequence doesn't show any significant nucleotide level sequence similarity in any other bacterial genus and on the host genome, thereby reducing the possibility of a cross-reactivity. Hence, these elements are ideal candidates for targeting pathogenic *Streptococcus pneumoniae*. Also, literature evidence points out that these repeated regions are previously identified as SPRITE elements (*Streptococcus pneumoniae* Rho-Independent Terminator-like Element) (e.g., Croucher, Nicholas J., et al. "Identification, variation and transcription of pneumococcal repeat sequences." BMC genomics 12.1 (2011): 120). In addition to that, the identified set of nucleotide sequences, referred from now as RSTREP (FIG. 7), are not specific to a single strain of *Streptococcus pneumoniae* but occur in all pathogenic strains of this pathogen. Thus, even if the strain level information of the *Streptococcus pneumoniae* causing the infection is not available, the method can be utilized to target the pathogen.

According to the present embodiment, the method of treating *Streptococcus pneumoniae* infection includes following steps:

Step I—Identifying sequence stretches which repeat multiple times on a pathogenic genome RSTREP. Herein, conserved nucleotide repeat elements were identified on *Streptococcus pneumoniae* genome by taking sequence stretches of predefined length Rn (30-60 in this embodiment), keeping the difference in the start position of $R_{ni+1}$ and $R_{ni}$ as 5 nucleotide (As shown in FIG. 2A). In this implementation, stretches of sequences were aligned within the genome by local alignment (as implemented in PILER software) to find the location of these elements in all sequenced *Streptococcus pneumoniae* genomes. Sequence based search utilizing any other alignment or repeat finding tools can also be utilized for this purpose.

Step II—Identification and annotation of gene neighborhood of repeat elements.

On each *Streptococcus pneumoniae* genome where repeat elements RSTREP occur, 10 flanking genes both upstream and downstream were found on each strand (+ and −) of DNA on the nucleotide genome sequence of the pathogen. Functional annotation of these genes was performed using HMM search with PFAM as the database. Other methods for gene annotation are also within the scope of this invention. Functional categorization of these genes on the basis of pathways they are involved in was carried out using literature mining. The broad categories have been discussed in Table 1.

TABLE 1

Summary of proteins in vicinity conserved sequence RSTREP in *Streptococcus pneumoniae*

| Category | Genes | Function |
|---|---|---|
| Pathogenic/VirueInce Proteins | | |
| Toxins | pneumococcal histidine triad protein B | Invokes host immune response through complement system |
| | PepO (Endopeptidase O) | Involved in a adhesion to host cells |
| | Haemolytic protein | Disruption of host RBCs |
| | hsa | Cell wall anchor protein |
| Antibiotic Resistance | metallo-beta-lactamase | Resistance against lactam rings |
| | Penicillin-binding proteins | Involved in penicillin resistance |
| | Penicillinase Regulator | Controls in penicillin resistance |
| | Lactonase | Quorum quencher inhibitor |
| Biofilm Formation | QueC/F | Queuosine biosynthesis |
| | Cps | Capsular polysaccharide biosynthesis protein |
| DNA Repair machinery | UvrD_C | DNA repair proteins |
| | RadC | DNA repair protein |
| | RuvA_N | Holliday junction DNA helicase |
| | RecU | Holliday junction endonuclease |
| | MutL_C | Mismatch repair proteins |
| | DNA gyrase | |
| | DNA topoisomerase | Unwinds DNA supercoiling |
| Survival Proteins | | |
| Host Immune evasion | CutC | Copper Resistance proteins |
| | PepO (Endopeptidase O) | Innate immunity evasion |
| | TroA | Manganese acquisition in host cells |
| Stress Response | CsbD | Stress response protein |
| | Usp | Universal stress response protein |
| Essential Proteins | | |
| Essential Proteins | DNA polymerase III | Involved in DNA synthesis |
| | Polysacchride biosynthesis | Cell wall biosynthesis |
| | Muramyl ligase | Involved in cell wall synthesis |
| | LicD | Involved in teichoic acid production. |
| | lactate dehydrogenase | Converts lactate to pyruvate |

Step III—Targeting the repeat element sequence near the pathogenic regions. Herein, the identified nucleotide repeat sequences were checked for potential secondary structure formation such as hairpin loops. In this case, the RSTREP element sequences are found to be palindromic and may form a hairpin loop structure indicating their role in regulation of transcription. These loops may either form at DNA level or at the ends of their mRNA during DNA transcription. The hairpin loop in the mRNA could be involved in prevention of the early decay of mRNA, resulting in higher protein formation of the virulence genes which are in the vicinity of these palindromic elements. Reduction in pathogenicity can be achieved by decreasing the stability of mRNA corresponding to these virulent genes which can be attained by removing the hairpin loops. If hairpin loop formation takes place at DNA level it might regulate DNA supercoiling concatenation.

The hairpin loop is not followed by a poly a tail in RSTREP indicating it might not be working as transcription terminator. The strategy for targeting such nucleotide repeat sequence is discussed below. The nucleotide repeat sequences can be targeted as discussed in case I using various laboratory accepted methods. One possible strategy involves a construct containing target sequence, an enzyme capable of cutting at the region where target sequence binds (nickase in one embodiment) and another enzyme capable of recognizing the nick and cutting off flanking regions (exonuclease in one embodiment)

Step IV—A preventive and therapeutic strategy. The method described above may be used in combination with one or more conventionally known methods of treating *Streptococcus pneumoniae* infections to form an effective strategy for preventive and therapeutic measures. For example, as a preventive measure the present disclosure may be used in combination with one or more antibacterial agents. As a therapeutic measure the present method may be used in combination with one or more antimicrobial methods available in the art. In one of the example, the method may be used along with antibiotics used in treating *Streptococcus pneumoniae* infections such as cefotaxime, ceftriaxone or vancomycin etc. and vaccines against essential proteins such as 13-valent pneumococcal conjugate vaccine (PCV13) and pneumococcal polysaccharide vaccine (PPSV23) for therapeutic purposes.

The administered construct might contain enzymatic machinery to cleave the set of nucleotide repeat sequences as shown in FIG. 8 as well as removal of the flanking virulent and the essential genes in *Streptococcus pneumoniae* genome as depicted in FIG. 9.

The embodiments of present disclosure herein provide a system and method for treating the antibiotic resistant pathogenic infection.

The embodiments of present disclosure herein address the problem of combating pathogenic infections. The present disclosure provides strategies to combat pathogenic infections, including those caused by multi-drug resistant (MDR) and extensively drug resistant (XDR) strains. The strategy involves identifying potential target sites in a pathogen which can be utilized to compromise its multiple functions at the same time. The embodiment, thus provides a combination of targeting multiple important genes of pathogens in addition to antimicrobials and biofilm inhibitors which have a better potential in targeting the pathogens. Moreover, the embodiments herein further provide identifying targets in pathogens with minimal cross-reactivity with commensals as well as host and targeting multiple regions on the genome simultaneously making it difficult for the pathogens to restructure the machinery back again.

The embodiments of present disclosure herein provide a method and system for combating antimicrobial resistant pathogens.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of antimicrobial resistance as can be observed in multi drug resistant and extensively drug resistant pathogens. The embodiment provides a system and method to identify a nucleotide sequence stretch on a pathogen genome which occurs as a multiple repeat on the genome and occupies distant locations. The embodiment further emphasizes that such a nucleotide sequence should be specific to the pathogenic strains of target pathogen (species or genus) and should not occur more than twice within the genome of commensal strains of the pathogen or in other genera. The nucleotide repeat sequence can be used to target multiple regions of pathogen genome thereby debilitating its important functions. The system involves administration of an engineered polynucleotide construct containing enzymatic machinery for binding the nucleotide repeat sequence on pathogen genome and nicking and cleaving the genome after recognition of target site.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words “comprising,” “having,” “containing,” and “including,” and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms “a,” “an,” and “the” include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term “computer-readable medium” should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A method for identification of candidate target sites for combating pathogenic infection due to pathogens, the method comprising:
 obtaining a sample from an infected area;
 extracting DNA from the obtained sample using DNA extraction methods;
 sequencing the isolated DNA using a sequencer;
 detecting a pathogen from the sequenced DNA;
 identifying a set of nucleotide repeat sequences in the extracted DNA which are occurring more than a predefined number of times in a pathogen genome,
 wherein the set of nucleotide repeat sequences corresponding to one or more than one strain of the pathogen,
 wherein the set of nucleotide repeat sequences are found in multiple copies at distant locations on the genomes of all pathogenic strains of a candidate genus or species and these nucleotide repeat sequences do not show more than the two-nucleotide sequence similarity based match to genome sequences corresponding to genera or species other than the genome sequences of the pathogens belonging to the candidate genus or species or with genomes of commensal strains within the candidate genus or species,
 wherein the set of nucleotide repeat sequences are selected if the set of nucleotide repeat sequences are present only in the candidate genus of the pathogen,
 wherein distant locations refer to a distance greater than a predetermined number of nucleotide base pairs;
 identifying a set of neighborhood genes present upstream and downstream of the set of nucleotide repeat sequences;
 categorizing the set of neighborhood genes according to their functional roles in the pathogen based on their involvement in pathways;
 testing the presence of a secondary structure in the identified set of nucleotide sequences;
 preparing and administering an engineered polynucleotide construct on the infected area to treat the pathogenic infection by cleaving the set of nucleotide repeat sequences and removing flanking genes,
 wherein the engineered polynucleotide construct is administered to the target bacterial cell using a bacterial, a plasmid or a viral vector,
 wherein the engineered polynucleotide construct is in the form of an oral medicine, topical creams, nasal administration, aerosol sprays, an injectable cocktail,
 wherein the engineered polynucleotide construct comprises:
 one or more of the identified set of nucleotide repeat sequences occurring in multiple copies at dispersed locations on candidate pathogen genomes of one or more of *Streptococcus pneumonia, Staphylococcus epidermidis, Mycobacterium tuberculosis, Pseudomonas aeruginosa, Klebsiella pneumoniae, Staphylococcus aureus, Xanthomonas axonopodis, Clostridium* genomes, wherein the set of nucleotide repeat sequences comprises one or more of a Sequence ID 001, and reverse complement of the Sequence ID 001,
 a first enzyme capable of nicking and cleaving the identified set of nucleotide repeat sequences, and
 a second enzyme capable of removal of a set of neighborhood genes flanking the set of nucleotide repeat sequences;
 assessing the efficacy of the administered construct; and
 re-administering the engineered polynucleotide construct repetitively in case the pathogen presence is detected at the infected area post administering, till the pathogen is completely eliminated,
 wherein the engineered polynucleotide construct targets the identified set of nucleotide repeat sequences on the pathogen genome along with important functional genes flanking the identified set of nucleotide repeat sequences to debilitate multiple important functions of the pathogen simultaneously and disrupt the overall functioning of the pathogen to carry out changes including gene silencing, gene recombination, gene substitution with a new function,
 wherein the important functional genes refer to the genes in pathogens which encode for proteins which are critical for survival, pathogenicity, interaction with the host, adherence to the host or for the virulence of bacteria, and
 wherein the minimum predefined number of genes to be considered in genomic neighborhood is 10.

2. The method according to claim 1 wherein the sample obtained from the infected area is one or more of fecal matter, blood, urine, a tissue biopsy or an environmental samples.

3. The method according to claim 1 wherein the DNA extraction methods comprise standardized laboratory protocols including DNA isolation and extraction kits.

4. The method according to claim 1, wherein sequenced microbial data comprises sequences obtained from next generation sequencing platforms comprising marker genes including 16S rRNA, Whole Genome Shotgun (WGS) sequences, sequences obtained from a fragment library, sequences from a mate-pair library or a paired-end library based sequencing technique, a complete sequence of the pathogen genome or a combination thereof, wherein the pathogen detection in the sample depends on identification of taxonomic groups from the sequences.

5. The method according to claim 1, wherein the engineered polynucleotide construct is inserted into vectors which allow insertion of external DNA fragments, wherein the engineered polynucleotide construct is carried by plasmid or phage based cloning vectors, wherein the engineered polynucleotide construct further comprises a bacteria-specific promoter sequence, a terminator sequence, and a stretch of Thymine nucleotides which is transcribed into a polyA tail for stabilizing the mRNA transcripts corresponding to each enzyme, and wherein promoters and terminators specific to bacteria are utilized in the engineered polynucleotide construct.

6. The method according to claim 1 wherein the engineered polynucleotide construct comprises a CRISPR-Cas system, comprising:

a CRISPR enzyme, a guide sequence capable of hybridizing to an identified target sequence repeated within the pathogen genome, a tracr mate sequence, and a tracr sequence, wherein the guide sequence, the tracr mate and the tracr sequences are linked to one regulatory element of the engineered polynucleotide construct while the CRISPR enzyme is linked to another regulatory module within the vector.

7. The method according to claim 1, wherein the step of identifying the set of nucleotide repeat sequences further comprises:

selecting sequence stretches of a predefined length Rn from the genomes of strains of the pathogen with a difference in a start position of two consecutive nucleotide stretches Rni+1 and Rni as nucleotides, wherein the predefined length refers to the length of the stretch of nucleotide sequence picked from the complete nucleotide sequence of a bacterial genome;

aligning the stretch of sequences within the genome of the candidate genus or species or within the genomes of all strains of the candidate genus or species; and identifying the set of nucleotide repeat sequences occurring more than 10 times at distant locations on the bacterial genome as the set of nucleotide sequences.

8. The method according to claim 1, wherein the distant locations refer to the distance greater than 10000 nucleotide base pairs.

9. The method according to claim 1, wherein the identified nucleotide repeat sequences are in a genomic neighborhood of or flanking genes encoding proteins with functions within the pathogen genome, wherein the genomic neighborhood refers to regions lying within a predefined number of genes to a selected nucleotide repeat sequence or the reverse complement of the selected nucleotide repeat sequence on the candidate pathogen genomes or lying within a distance of a predefined number of bases with respect to the selected nucleotide repeat sequence on the pathogen genome.

10. The method according to claim 1, wherein a sequence matching is performed by processor-implemented tools for nucleotide sequence alignment comprising BLAST or Burrows wheeler alignment tool.

11. The method according to claim 1, wherein non-culturable taxonomic groups or pathogens within the sample collected from an environment are obtained by amplification of marker genes including 16S rRNA within bacteria.

12. The method according to claim 1, wherein information and detection of non-culturable taxonomic groups or pathogens within the sample is obtained by the binning of whole genome sequencing reads into various taxonomic groups using a plurality of methods including sequence similarities as well as a plurality of methods using supervised and unsupervised classifiers for taxonomic binning of metagenomics sequences.

* * * * *